(12) United States Patent
Katzman

(10) Patent No.: US 7,884,135 B2
(45) Date of Patent: Feb. 8, 2011

(54) MODAFINIL-BASED TREATMENT FOR PREMATURE EJACULATION

(75) Inventor: Daniel E. Katzman, Newton, MA (US)

(73) Assignee: NeuroHealing Pharmaceuticals, Inc., Newton, MA (US)

(*) Notice: Subject to any disclaimer, the term of this patent is extended or adjusted under 35 U.S.C. 154(b) by 0 days.

(21) Appl. No.: 12/310,175

(22) PCT Filed: Aug. 13, 2007

(86) PCT No.: PCT/US2007/017948

§ 371 (c)(1),
(2), (4) Date: Feb. 13, 2009

(87) PCT Pub. No.: WO2008/021341

PCT Pub. Date: Feb. 21, 2008

(65) Prior Publication Data

US 2009/0318559 A1  Dec. 24, 2009

Related U.S. Application Data

(60) Provisional application No. 60/837,474, filed on Aug. 14, 2006.

(51) Int. Cl.
*A61K 31/165* (2006.01)
(52) U.S. Cl. .................................................. 514/618
(58) Field of Classification Search ................. 514/618
See application file for complete search history.

(56) References Cited

U.S. PATENT DOCUMENTS

| | | | |
|---|---|---|---|
| 4,177,290 A | 12/1979 | Lafon | |
| 4,927,855 A | 5/1990 | Lafon | |
| 5,612,379 A | 3/1997 | Laurent | |
| 5,700,478 A | 12/1997 | Biegajski et al. | |
| 6,177,096 B1 | 1/2001 | Zerbe et al. | |
| RE37,516 E | 1/2002 | Grebow et al. | |
| 6,348,500 B1 | 2/2002 | Fu | |
| 6,465,519 B2 | 10/2002 | Fu | |
| 6,489,363 B2 | 12/2002 | Jacobs et al. | |
| 6,552,024 B1 | 4/2003 | Chen et al. | |
| 6,756,051 B1 | 6/2004 | Chen et al. | |
| 6,875,893 B2 | 4/2005 | Largeau et al. | |
| 2001/0034373 A1 | 10/2001 | Miller et al. | |
| 2002/0098240 A1 | 7/2002 | Jacobs et al. | |
| 2003/0171439 A1 | 9/2003 | Lawyer et al. | |
| 2004/0105891 A1 | 6/2004 | Bentolila et al. | |
| 2004/0170683 A1 | 9/2004 | Sherman | |
| 2004/0229942 A1 | 11/2004 | Hassman et al. | |
| 2006/0241320 A1 | 10/2006 | Neckebrock et al. | |
| 2006/0252835 A1 | 11/2006 | Broquaire et al. | |
| 2007/0021510 A1 | 1/2007 | Hickey et al. | |
| 2007/0065517 A1 | 3/2007 | Heacock et al. | |
| 2007/0293702 A1 | 12/2007 | Braude et al. | |
| 2008/0031939 A1 | 2/2008 | Braude et al. | |
| 2008/0058424 A1 | 3/2008 | Covari et al. | |

FOREIGN PATENT DOCUMENTS

| | | | |
|---|---|---|---|
| EP | 1 291 016 A1 | 3/2003 | |
| WO | WO 02/30413 A1 | 4/2002 | |
| WO | WO 2006/032146 | 3/2006 | |
| WO | WO 2007/013962 | 2/2007 | |

OTHER PUBLICATIONS

Waldinger et al., J. Sex. Med., 2005;2:121-131.*
Ninan et al., Journal of Clinical Psychiatry, 2004;65(3):414-420 (Abstract only).*
International Preliminary Report on Patentability for international application No. PCT/US2007/017948 (Feb. 26, 2009).
International Preliminary Search Report for international application No. PCT/US2007/017948 (Jul. 3, 2008).
Written Opinion of the International Searching Authority for international application No. PCT/US2007/017948 (Jul. 3, 2008).
Bi et al., Preparation and Evaluation of a Compressed Tablet Rapidly Disintegrating in the Oral Cavitiy, *Chem. Pharm. Bull.* (Tokyo), 44: 2121-2127 (1996).
Birudaraj et al., Buccal Permeation of Buspirone: Mechanistic Studies on Transport Pathways, *J. Pharm. Sci.*, 94: 70-78 (2005).
Cilurzo et al., Fast-dissolving mucoadhesive microparticulate delivery system containing piroxicam, *Eur. J. Pharm. Sci.*, 24(4): 355-361 (2005).
Dinges et al., Pharmacodynamic effects on alertness of single doses of armodafinil in healthy subjects during a nocturnal period of acute sleep loss, *Curr. Medical Research and Opinions*, 22: 159-167 (2006).
Donovan et al., Chiral Analysis of *d*- and *l*-Modafinil in Human Serum: Application to Human Pharmacokinetic Studies, *Ther. Drug. Monit.*, 25(2): 197-202 (2003).

(Continued)

*Primary Examiner*—San-ming Hui
(74) *Attorney, Agent, or Firm*—Leon R. Yankwich; David G. O'Brien; Yankwich & Associates, P.C.

(57) ABSTRACT

Methods and compositions comprising modafinil are described for treating premature ejaculation in a male individual.

12 Claims, No Drawings

OTHER PUBLICATIONS

Duteil et al., Central x/-adrenergic stimulation in relation to the behaviour stimulating effect of modafinil; studies with experimental animals, *Eur. J. Pharmacol.*, 180: 49-58 (1990).

Fu et al., Orally Fast Disintegrating Tablets: Developments, Technologies, Tast-Masking and Clinical Studies, *Crit. Rev. Ther. Drug Carrier Syst.*, 21(6): 433-475 (2004).

Hass et al., Developments in the area of bioadhesive drug delivery systems, *Expert Opin. Biol. Ther.*, 2(3): 287-298 (2002).

Ishikawa et al., Pharmacokinetics of Acetaminophen from Rapildy Disintegrating Compressed Tablet Prepared Using Microcrystalline Celluose (PH-M-06) and Spherical Sugar Granules[1]), *Chem. Pharm. Bull.* (Tokyo), 49: 230-232 (2001).

Laumann et al., Sexual Dysfunction in the United States: Prevalence and Predictors, *JAMA*, 281: 537-544 (1999).

Looney et al., Differential effects of simultaneous or sequential administration of paroxetine and WAY-100,635 on ejaculatory behavior, *Pharmacol. Biochem.*, 82: 427-433 (2005).

Pattij et al., Animal Models of Ejaculatory Behavior, *Curr. Pharm. Des.*, 11(31): 4069-4077 (2005).

Price et al., Single-Dose Pharmacokinetics of Sublingual Versus Oral Administration of Micronized 17β-Estradiol, *Obstet. Gynecol.*, 89: 340-345 (1997).

Prisinzano et al., Synthesis and determination of the absolute configuration of the enantiomers of modafinil, *Tetrahedron: Asymmetry*, 15: 1053-1058 (2004).

PROVIGIL® Patient Information Leaflet (Cephalon, Inc., West Chester, PA, 2004).

Rapid-Dissolve Technology: An Interview with Loyd V. Allen, Jr., PhD, RPh, *International Journal of Pharmaceutical Compounding*, 7(6): 449-450 (2003).

Robertson et al., Clinical Pharmacokinetic Profile of Modafinil, *Clin. Pharmacokinet.*, 42: 123-137 (2003).

Salamat-Miller et al., The use of mucoadhesive polymers in buccal drug delivery, *Adv. Drug Deliv. Rev.*, 57(11): 1666-1691 (2005).

Saletu et al., Differential Effects of a New Central Adrenergic Agonist—Modafinil—and D-Amphetamine on Sleep and Early Morning Behaviour in Young Healthy Volunteers, *Int. J. Clin. Pharm. Res.*, 9: 183-195 (1989).

Sharlip, J., Diagnosis and Treatment of Premature Ejaculation: The Physician's Perspective, *J. Sex. Med. Supp.*, 2: 103-109 (2005).

Smart, The basics and underlying mechanisms of mucoadhesion, *Adv. Drug Deliv. Rev.*, 57(11): 1556-1568 (2005).

Türker et al., Nasal route and drug delivery systems, *Pharm. World Sci.*, 26(3): 137-142 (2004).

Ugwoke et al., Nasal mucoadhesive drug delivery: Background, applications, trends and future perspectives, *Adv. Drug Deliv. Rev.*, 57(11): 1640-1650 (2005).

Waldinger, Lifelong premature ejaculation: definition, serotonergic neurotransmission and drug treatment, *World J. Urol.*, 23(2): 115-118 (2005).

Watanbe et al., New Compressed Tablet Rapildy Disintegrating in Saliva in the Mouth Using Crystalline Cellulose and a Disintegrant, *Biol. Pharm. Bull.*, 18: 1308-1310 (1995).

Wisor et al., Dopaminergic role in Stimulant-Induced Wakefulness, *J. Neuroscience*, 21(5): 1787-1794 (2001).

Wong et al., A Double-Blind, Placebo-Controlled, Ascending-Dose Evaluation of the Pharmacokinetics and Tolerability of Modafinil Tablets in Healthy Male Volunteers, *J. Clin. Pharmacol.*, 39: 30-40 (1999).

Wong et al., Open-Label, Single-Dose Pharmacokinetic Study of Modafinil Tablets: Influence of Age and Gender in Normal Subjects, *J. Clin. Pharmacol.*, 39: 281-288 (1999).

Woodley, J., Bioadhesion, *Clin. Pharmacokinet.*, 40(2): 77-84 (2001).

EPO Communication dated Nov. 17, 2009, enclosing Extended European Search Report, supplemental EP search report, and the EP search opinion dated Nov. 5, 2009, issued in EP Application No. 07 811305.7.

EPO Communication pursuant to Article 94(3) EPC dated Jan. 29, 2010, issued in EP application No. 07 811305.7, with attached European Search Opinion and Supplementary European Search Report dated Nov. 5, 2009.

Marson et al., "Effects of NHO2D on Ejaculation Latency and Sexual Behavior in Rats", The Journal of Urology, 181(4) Supplement: 241 (Abstract No. 672) (Apr. 27, 2009).

Marson et al., "The Effects of Oral Administration of D-Modafinil on Male Rat Ejaculatory Behavior", J. of Sex. Med., vol. 7, Issue 1, pt 1: 70-78 (2009).

Waldinger, M.D., "Use of Psychoactive Agents in the Treatment of Sexual Dysfunction", CNS Drugs, 6(3): 204-216 (1996).

* cited by examiner

MODAFINIL-BASED TREATMENT FOR PREMATURE EJACULATION

CROSS-REFERENCE TO RELATED APPLICATIONS

This application is a United States national stage filing under 35 U.S.C. §371 of international application No. PCT/US2007/017948, filed Aug. 13, 2007, designating the U.S., which claims priority to U.S. Provisional Application No. 60/837,474, filed Aug. 14, 2006.

FIELD OF THE INVENTION

This invention is in the field of sexual dysfunction. In particular, this invention provides compositions and methods for delaying ejaculation and treating premature ejaculation during sexual activity.

BACKGROUND OF THE INVENTION

The three major forms of male sexual dysfunction are premature ejaculation (PE), erectile dysfunction (ED), and decreased libido. The American Urological Association defines premature ejaculation as ejaculation that occurs sooner than desired, either before or shortly after penetration, causing distress to either one or both partners (*Guideline on the Pharmacologic Management of Premature Ejaculation*, American Urological Association, 2004). The dysfunction is classified as either lifelong (primary) or acquired (secondary). Premature ejaculation is among the most prevalent of male sexual complaints. A survey has estimated that PE affects approximately 25% to 30% (about one in five to about one in three) of men of all ages (see, Laumann et al., *JAMA*, 281: 537-544 (1999)). In the United States, approximately 25 million men between the ages of 18 and 59 experience PE. Whatever the actual figures, persistent PE can leave sexual partners feeling unsatisfied or unfulfilled, can cause stress or embarrassment to the affected male individual, and can lead to a deterioration of the intimate relationship between partners.

Treatments for PE include psychotherapeutic/behavioral therapies and pharmacological treatments (for a review, see, Sharlip, *J. Sex Med.*, Supp. 2: 103-109 (2005)). Among the pharmacological agents reported to provide some desirable delay in ejaculation in the male patient are topical anesthetics, non-selective serotonin reuptake inhibitors (SRIs), selective serotonin reuptake inhibitors (SSRIs), and phosphodiesterase-5 inhibitors (PDE-5). Topical anesthetics, e.g., preparations containing benzocaine or a lidocaine-prilocaine combination, are applied to the penis to diminish sensitivity and delay ejaculation. However, topically applied anesthetics can cause irritation to either or both partners or result in an undesired hypoesthesia that prevents orgasm.

Selective serotonin reuptake inhibitors (SSRIs) are a class of drugs used to treat depression and various anxiety or personality disorders. SSRIs have also been reported to delay or inhibit sexual climax and to delay ejaculation. Such sexual side effects, including delay of ejaculation, have been reported for such well known antidepressants as fluoxetine (commercially available as PROZAC®, Eli Lilly and Company, Indianapolis, Ind.), sertraline (commercially available as PAXIL®, GlaxoSmithKline plc, London, United Kingdom), paroxentine (commercially available as ZOLOFT®, Pfizer Inc., New York, N.Y.), and dapoxetine (Alza Corporation, Mountain View, Calif.). Accordingly, SSRIs have also been the focus for developing treatments for PE. Similar sexual side effects have been noted in patients treated with the tricyclic antidepressant clomipramine (e.g., ANAFRANIL®, Novartis International AG, Basel, Switzerland), which has also been used to treat PE.

Use of most antidepressants, such as currently employed SRIs or SSRIs, to treat PE has typically been proposed to involve a chronic continuous dosing regimen analogous to those employed in treating depression or severe personality disorders. However, chronic dosing regimens for SRIs and SSRIs increase the risk of accumulating one or more side effects, including undesired anti-cholinergic effects, reduced sexual desire, genital anesthesia, headache, nausea, sweating, and dizziness. The risk or emergence of such side effects is justified in view of the benefit for treating chronic depression, abnormal anxiety, or severe personality disorders. In cases in which dosing of an SSRI has been used to treat PE on an acute or "as needed" (prn) basis, the efficacy of the drug has been undesirably diminished. With chronic continuous dosing, even when administered at doses below those normally used to treat depression, psychoactive drugs such as SSRIs may eventually cause one or more adverse side effects that contraindicate their continued use or that ultimately diminish compliance by patients who do not require treatment for debilitating depression or severe personality disorders.

Dapoxetine is the first SSRI drug that was specifically developed to treat PE. The pharmacokinetics of dapoxetine, e.g., faster acting and faster clearance than other SSRIs, were seen as particularly desirable for the development of an orally administrable dapoxetine tablet that could be taken one to three hours before sexual activity, thereby providing an "on demand" or "as needed" (prn) treatment that eliminated the need for the chronic continuous dosing employed for off-label uses of other SSRI antidepressants. Side effects are similar to those found with other SSRI drugs with nausea, diarrhea, and dizziness being among the most prevalent in clinical trials. In October 2005, the United States Food and Drug Administration issued a not-approvable letter for a new drug application for dapoxetine treatment of PE.

Clearly, needs remain for more effective pharmacologic treatments for PE.

SUMMARY OF THE INVENTION

The invention solves the above problems by providing methods and compositions for treating premature ejaculation (PE) in a male individual comprising administering to the individual an effective amount of modafinil (benzhydrylsulfinyl acetamide; 2-[(diphenylmethyl)sulfinyl]acetamide) to delay, but not prevent, ejaculation during sexual intercourse.

Modafinil may be formulated as the racemic mixture or other combination of its l- and d-enantiomers. L-modafinil (R-(−)-enantiomer) has a half-life ($T_{1/2}$) in the human body of approximately 10 hours to 14 hours compared with 3 hours to 4 hours for d-modafinil (S-(+)-enantiomer). Accordingly, methods and compositions described herein may comprise a modafinil component comprising different combinations of the l- and d-enantiomers of modafinil to provide the desired pharmacologic effect for varying lengths of time.

In a preferred embodiment, methods and compositions described herein comprise a modafinil component that comprises greater than 50% by weight and up to 100% by weight d-modafinil. More preferably, the modafinil component of methods and compositions described herein is 100% by weight d-modafinil to provide the shortest duration of the desired pharmacological activity of modafinil.

In another preferred embodiment, compositions and methods as described herein comprise a non-particulate modafinil.

Modafinil may be formulated for administration to treat PE in a male individual by any of a variety of routes or modes including, without limitation, sublingually, buccally, orally for swallowing into the stomach, topically (including transdermally), nasally, intravenously, subcutaneously, intramuscularly, and rectally.

In another embodiment, the invention provides a pharmaceutical composition comprising modafinil and a pharmaceutically acceptable carrier for use in methods described herein to treat PE.

In a preferred embodiment, a pharmaceutical composition is formulated to provide the desired pharmacological activity of modafinil to an individual as rapidly as possible using a route of administration that avoids ingestion into the gut and hepatic first-pass metabolism.

In another preferred embodiment, a pharmaceutical composition used in the methods described herein is formulated in a dosage form selected from the group consisting of a fast disintegrating tablet; a lyophilized preparation; a film, which is particularly well-suited for sublingual or buccal administration; and a formulation for intranasal administration. More preferably, a composition is formulated for administration to a mucosal membrane (e.g., oral, nasal, or rectal mucosa) of an individual. Even more preferably, a composition is mucoadhesive.

Pharmaceutical compositions comprising modafinil as described herein may also contain one or more additional ingredients including, but not limited to, a mucoadhesive compound, a buffering agent, a plasticizing agent, a stabilizing agent, a taste-masking agent, a flavoring agent, a coloring agent, an antiseptic, an inert filler agent, a preservative, and combinations thereof.

Also provided are kits and devices that comprise modafinil for use in treating PE. Devices for administering modafinil to treat PE in an individual include, but are not limited to, an inhaler, a nebulizer, and a disposable applicator. Preferred forms of a disposable applicator include, but are not limited to a transdermal patch, a swab, a sponge, and a strip. Such devices deliver a sufficient amount of modafinil or a modafinil composition as described herein to delay ejaculation by an individual during sexual intercourse. Preferably, the modafinil present in or on a device as described herein is greater than 50% by weight d-modafinil and more preferably about 100% by weight d-modafinil. Preferably, the modafinil present in or on a device described herein is a non-particulate modafinil.

DETAILED DESCRIPTION OF THE INVENTION

The invention provides methods and compositions for treating premature ejaculation (PE) in a male individual by administering modafinil to the individual prior to sexual intercourse. Modafinil may be formulated and used as described herein to provide a relatively rapid onset of the desired effect in an "on demand" or "as needed" (pm) basis (also referred to as an "acute" basis) without the need for a period of chronic continuous dosing (e.g., daily for a week or more) to build up and maintain a certain level of the drug in the circulation or tissue before the desired benefit of delaying ejaculation during sexual intercourse is obtained.

A composition or method described herein as "comprising" (or "comprises") one or more named elements or steps is open-ended meaning that the named elements or steps are essential, but other elements or steps may be added within the scope of the composition or method. To avoid prolixity, it is also understood that any composition or method described as "comprising" one or more named elements or steps also describes the corresponding, more limited, composition or method "consisting essentially of" (or "consists of") the same named elements or steps, meaning that the composition or method includes the named essential elements and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and close-ended composition or method "consisting of" (or "consists of") the named elements or steps to the exclusion of any other element or step. In any composition or method disclosed herein, known or disclosed equivalents of any named essential element or step may be substituted for that element or step, respectively.

The term "modafinil" is synonymous with benzhydrylsulfinyl acetamide and 2-[(diphenylmethyl)sulfinyl]acetamide as described in U.S. Pat. Nos. 5,612,379 and 6,489,363 (incorporated herein by reference). The compound was originally identified as a member of a genus of acetamide derivatives developed by the Laboratoire L. Lafon in the 1970s (see, e.g., U.S. Pat. No. 4,177,290). Modafinil is structurally distinct from various groups of classic central nervous system (CNS) stimulants and also has a distinctly different mode of action that has yet to be fully elucidated. The following formula represents the neutral (free) base form of modafinil:

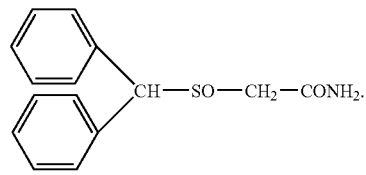

The sulfur in modafinil is a chiral center. Accordingly, modafinil may exist as a racemic mixture (racemate) or as individual enantiomers. Individual enantiomers of modafinil may be resolved by methods known in the art (see, e.g., Donovan et al., *Ther. Drug Monit.*, 25(2): 197-202 (2003)). It is also understood that the terms "modafinil", "benzhydrylsulfinyl acetamide", and "2-[(diphenylmethyl)sulfinyl]acetamide" encompass the various organic and inorganic acid salt forms of the free base. Preparations and modes of delivery of modafinil may include one or more of those that are known in the treatment of other disorders (see, e.g., U.S. Pat. No. 5,612,379; U.S. Reissue Pat. No. RE37,516 E; U.S. Pat. No. 6,489,363). In addition, methods and compositions of the invention comprising modafinil, as described herein, may alternatively comprise, instead of modafinil, a pro-drug of modafinil, i.e., a compound that is metabolized to modafinil when administered to an individual. Functionally equivalent modified forms of modafinil, as well as derivates, analogues, and mimics of modafinil may also be used in accordance with the teachings herein.

The precise pharmacological mechanism of action of modafinil on the central nervous system (CNS) is unclear (see, e.g., *Physician's Desk Reference*, 61st ed. (Thomson, Montvale, N.J., 2007), pages 988-993). For example, it has been suggested that modafinil modulates the central postsynaptic alpha-adrenergic receptor without participation of the dopaminergic system (see, e.g., Duteil et al., *Eur. J. Pharmacol.*, 180: 49-58 (1990)). However, another study has reported that modafinil increased extracellular dopamine and that dopamine transporter knock-out mice were unresponsive to the action of modafinil (Wisor et al., *J. Neuroscience,* 21(5): 1787-1794 (2001)). The neuropsychopharmacological profile of modafinil has been distinguished from amphetamines (see, e.g., Saletu et al., *Int. J. Clin. Pharm. Res.,* 9:183-195 (1989)).

As mentioned above, modafinil is a racemic compound with a chiral center at its sulfur atom. Modafinil molecules exist as either of two optically active forms, i.e., "d-modafinil" (S-(+)-modafinil) and "l-modafinil" (R-(−)-modafinil). A commercially available formulation of the modafinil racemate is the orally administrable tablet PROVIGIL® (Cephalon, Inc., West Chester, Pa.), which is approved for use as a wakefulness-promoting agent to treat excessive daytime sleepiness (EDS) in individuals who suffer from narcolepsy (see, e.g., Wong et al., *J. Clin. Pharmacol,* 39: 3040 (1999); U.S. Reissue Pat. No. RE37,516 E). Such commercial tablets contain 100 mg or 200 mg of racemic modafinil. Recently, a formulation of the l-enantiomer of modafinil (NUVIGIL®, Cephalon, Inc., West Chester, Pa.) was approved in the United States for treatment of EDS as well. A recognized advantage of using modafinil to treat EDS is that modafinil is generally considered to have fewer side effects or side effects that are more readily treated than those associated with other drugs, such as the stimulant amphetamine and structurally related compounds that are known to exert an effect on the CNS.

The optical enantiomers of modafinil have similar pharmacological actions in animals. Both d-modafinil and l-modafinil have been reported to have the same pharmacological activity as the modafinil racemic compound in mice, however, pharmacokinetic studies of the racemic compound have shown that l-modafinil has a half-life ($T_{1/2}$) in the human body of approximately 10 hours to 14 hours compared with about 3 hours to 4 hours for d-modafinil. In addition, the elimination of d-modafinil has been reported to be three times faster than the elimination of l-modafinil. Owing to the differences in half-life and rate of clearance of the individual enantiomers, the use of racemic modafinil results in differences in the circulating levels of the two enantiomers. The amount of d-modafinil in the circulation can be three times less and of a shorter duration than that of l-modafinil. After a single oral dose, racemic modafinil is readily absorbed, reaching maximum plasma concentrations at 2 hours to 4 hours after administration (see, e.g., Wong et al., *J. Clin. Pharmacol.,* 39: 3040 (1999); Wong et al., *J. Clin. Pharmacol.,* 39: 281-288 (1999); Robertson et al., *Clin. Pharmacokinet.,* 42: 123-137 (2003); and Dinges et al., *Curr. Medical Research and Opinions,* 22: 159-169 (2006)).

The specific dose of modafinil administered to an individual to treat PE according to the invention will depend on any of a number of factors to be considered by an attending healthcare provider. Typically, a desired dose of modafinil should delay, but not prevent, ejaculation by an individual in a manner that improves the sexual experience of the individual with his partner with little or minimal effect on the ability of the individual to subsequently sleep, rest, or engage in other activities. Accordingly, dosing should provide the desired benefit with respect to treating PE and not be accompanied by a subsequent undesired effect of the drug, such as excessive wakefulness. Feedback from the individual after administration of a particular dose of modafinil is particularly useful to the healthcare provider in assessing and determining an appropriate dose for treating the individual for PE.

As noted above, dosing regimens for antidepressants, such as SSRIs, typically require chronic continuous, e.g., daily, administration in order to load and maintain a certain amount of the drug above a threshold amount in an individual in order to obtain and maintain a desired pharmacological activity. However, maintenance of a pharmacological level of an SSRI in an individual, even at a level below that used to treat chronic depression, is often accompanied by one or more adverse side effects that may not justify continued use for treatment of PE or may affect patient compliance with such treatment. In contrast, modafinil does not require prior loading and maintenance at a critical level in an individual to provide the desired pharmacological effect, i.e., delay in ejaculation during sexual activity, and thus can be formulated for use in an "on demand" or "as needed" (pm) basis. Accordingly, preferred methods and compositions described herein comprise modafinil formulated for pm dosing.

A "modafinil component", as used herein, refers to modafinil (racemate, individual modafinil enantiomer, combination of enantiomers) or a composition comprising modafinil. Preferably, a modafinil component employed in the methods and compositions described herein provides an individual with a desired delay in ejaculation during a period of sexual activity without a subsequent period of time in which the drug persists in the individual when not engaging in sexual activity. As the half-life of the l-enantiomer of modafinil is approximately three-times longer than that of the d-enantiomer (see, above), the modafinil component of methods and compositions described herein may be formulated to provide rapid delivery of modafinil and to control the length of time during which an individual has the benefit of the desired pharmacological activity of modafinil. Preferably, the methods and compositions described herein comprise a modafinil component that provides an individual with the desired effect for less than 11 hours, more preferably less than 10 hours, even more preferably for a period of about 30 minutes to about 5 hours, and most preferably for a period of about 30 minutes to less than 4 hours. Accordingly, preferred methods and compositions described herein comprise a modafinil component that is greater than 50% by weight and up to 100% by weight of the d-enantiomer of modafinil.

As noted above, currently available compositions of modafinil are in the form of tablets that are swallowed. Accordingly, modafinil may be formulated for oral administration for hepatic first-pass metabolism wherein the drug is swallowed and passes into the gastrointestinal tract (gut) and then into the liver before entering the systemic circulation. However, preferred routes of administration of modafinil for compositions and methods described herein are those that are likely to provide faster delivery and lower risk of degradation of modafinil than are associated with first-pass metabolism. Such preferred routes of administration of modafinil include, but are not limited to, sublingual, buccal, nasal, intravenous, subcutaneous, intramuscular, topical (including transdermal), and rectal modes of administration. Although delivery directly into the systemic circulation is more preferred than via the gut and liver (hepatic first-pass metabolism), the concentration of modafinil in the systemic circulation must be sufficient to ensure that an effective amount penetrates the blood-brain barrier and is delivered to the brain and CNS, which are the preferred targets of delivery. Administration to the mucosa of the nasal passages or of the mouth is particularly preferred owing to the fact that some of the capillaries underlying the mucosa provide a conduit directly to the circulation of the brain and CNS. Thus, formulations of modafinil for nasal or oral mucosal administration are not only convenient for pm dosing, but may provide the added benefit of requiring a lower concentration per dose owing to the enhanced efficiency of delivery to the brain and CNS.

Compositions described herein are preferably prepared in a delivery form to effectively delay, but not prevent, ejaculation during sexual intercourse. Compositions comprising modafinil as described herein may be formulated in any of a variety of solid, semi-solid, or liquid delivery forms ("dosage forms"). Non-particulate forms of modafinil are particularly preferred for use as the modafinil component of the compositions and methods described herein.

Generally, compositions used in the methods described herein may be formulated for administration to an individual by a specified route according to standard pharmaceutical protocols and texts (e.g., *Remington's Pharmaceutical Sciences,* 18th ed., Alfonso R. Gennaro, ed. (Mack Publishing Co., Easton, Pa. 1990)). Pharmaceutical compositions described herein preferably comprise a pharmaceutically acceptable carrier ("vehicle") and may also comprise any of a variety of other compounds that may be used in preparing a pharmaceutical composition for administration by a particular mode or route. By "pharmaceutically acceptable" is meant a material that is not biologically, chemically, or in any other way, incompatible with body chemistry and metabolism and also does not adversely affect the desired effective activity of the modafinil component or any other component in a composition described herein.

Compositions useful in the methods described herein for treating PE in an individual may include rapid onset (short $T_{max}$) and short term (short $T_{1/2}$) modafinil compositions as described in international application No. PCT/US2006/028150, filed Jul. 21, 2006 (available as PCT Publication No. WO 2007/013962; incorporated herein by reference). Preferably, such compositions comprise a modafinil component that is greater than 50% and up to 100% d-modafinil by weight.

Modafinil is essentially water insoluble (water solubility of about 0.4 mg/ml). Accordingly, preparation of compositions for use as described herein may employ various dry methods of preparation or the use of pharmaceutically acceptable, non-aqueous solvents. Nevertheless, in the course of preparing various compositions, it may be useful or necessary to use one or more pharmaceutically acceptable aqueous carriers including, but not limited to, water, physiological saline, and aqueous buffers.

The pharmaceutical compositions of this invention for oral administration may include, but are not limited to, liquids, lozenges, tablets, pills, capsules, caplets, oleaginous suspensions, syrups, elixirs, and sublingually or buccally administrable strips or films. Capsules, tablets, pills, and caplets may also be formulated for rapid disintegration (rapid dissolution). In the case of tablets for oral use, commonly used carriers include lactose and corn starch. Lubricating agents, such as magnesium stearate, may also be added.

Particularly preferred are compositions that deliver an effective amount of a modafinil component across a mucosal membrane to underlying tissues and blood vessels without ingestion into the gut (i.e., stomach and intestines) and subsequent hepatic first-pass metabolism. As much as 90% of modafinil delivered by ingestion of PROVIGIL® tablets is known to be eliminated by the liver in humans (see, PROVIGIL® package insert, Cephalon). Accordingly, preferred formulations permit administration of modafinil to mucosal tissues such as those lining the bottom of the mouth (e.g., sublingual administration), the cheeks of the mouth (buccal administration), the nasal passages (nasal administration), and the rectum (e.g., insertion of a suppository). Relatively rapid delivery and onset of activity are possible because such mucosa provide minimal barriers to the underlying blood vessels so that the drug can enter those blood vessels for more efficient delivery to the brain and CNS. As noted above, this is particularly efficient in the case of administration to the nasal and oral mucosa.

Dosage forms comprising modafinil that are to be administered to a mucosal membrane of an individual are preferably formulated to have a bioadhesive, i.e., mucoadhesive, property that permits the dosage form to preferentially adhere to a mucosal tissue surface and thereby keep the dosage form stationary at the point of application. This property is particularly desirable in dosage forms that are to be administered to the oral or nasal mucosa. In the case of a dosage form applied to the oral mucosa, mucoadhesion keeps the dosage form at a desired site of application (e.g., sublingual or buccal) where the dosage form will then dissolve and release modafinil for absorption by the underlying tissue and blood vessels without dislodging and being swallowed into the gut where modafinil would be subject to hepatic first-pass metabolism. Similarly, for dosage forms that are administered to the nasal mucosa, mucoadhesion is a desired feature to keep the dosage form on the mucosal surface where it will release modafinil for absorption by the underlying tissue and blood vessels. Mucoadhesion is a preferred property for keeping a dosage form stationary during use whether the dosage form dissolves and releases modafinil at a relatively rapid or relatively slow rate. A variety of natural and synthetic mucoadhesive compounds are known that may be incorporated into a dosage form described herein. Such mucoadhesive compounds include, but are not limited to, various mucoadhesive polymers such as chitosans, carbopols, carbomers, various thiolyated polymers, and lectins (see, e.g., Salamat-Miller et al., *Adv. Drug Deliv. Rev.,* 57(11): 1666-1691 (2005); Haas et al., *Expert Opin. Biol. Ther.,* 2(3): 287-298 (2002); Woodley, *Clin. Pharmacokinet.,* 40(2): 77-84 (2001); Ugoke et al., *Adv. Drug Deliv. Rev.* 57(11): 1640-1650 (2005); Smart, *Adv. Drug Deliv. Rev.,* 57(11): 1556-1568 (2005)).

Preferred compositions useful in the methods described herein may be formulated for administration to the sublingual and/or buccal tissue, where they rapidly dissolve or disintegrate to release an effective amount of modafinil that is then rapidly absorbed across the mucosa to underlying tissue and blood vessels to provide the desired pharmacologic activity, i.e., delay of ejaculation during sexual intercourse. Modafinil may be formulated in any of a variety of sublingually and buccally administrable delivery forms, including fast dissolving tablets, films ("strips" or "thin strips"), solutions, and suspensions. Particularly preferred are sublingually and buccally administrable films or strips that provide a relatively rapid delivery of non-particulate modafinil to an individual. Various types of films for delivering a drug have been described (see, e.g., U.S. Pat. No. 6,177,096; U.S. Pat. No. 5,700,478; U.S. Pat. No. 6,756,051; and U.S. Pat. No. 6,552,024). Such films are thin solid compositions that dissolve or disintegrate when they come into contact with saliva. Preferably, a film composition is formulated to be bioadhesive, i.e., mucoadhesive, which permits the film to readily adhere to an oral mucosal layer of tissue (e.g., sublingual, on the tongue, on the gums, buccal).

A film composition comprising modafinil may contain any of a variety of other pharmaceutically acceptable ingredients ("excipients") that may contribute or enhance one or more desirable properties in the film composition. Such excipients include, but are not limited to, a mucoadhesive compound, a buffering agent, a plasticizing agent, a stabilizing agent, a taste-masking agent, a flavoring agent, a breath freshening agent, a coloring agent, an antiseptic, an inert filler agent, a preservative, and combinations thereof.

Preferred film compositions comprising modafinil have a disintegration rate in the human mouth in the range of 1 second to 1200 seconds, more preferably 1 second to 600 seconds, even more preferably 1 second to 300 seconds, still more preferably 1 second to 150 seconds, and most preferably 1 second to 60 seconds. Particularly preferred are bioadhesive "fast-dissolving" film compositions that dissolve in less than about 1 minute, and preferably, in 1 second to 10 seconds when administered sublingually or buccally. Preferred bioadhesive (mucoadhesive) "slow-dissolving" types of films may take more than 1 minute, e.g., 5 to 30 minutes or 10 to 60 minutes, to dissolve when applied sublingually or buccally.

Preferably, films comprising a modafinil component as described herein will have a thickness in the range of less than 0.25 millimeters (mm) to 5 mm. Particularly preferred are films that are less than 0.25 mm in thickness.

Dosage forms of modafinil that are useful in the methods described herein include the BEMA™ (BioDelivery Sciences International, Morrisville, N.C.) orally-dissolvable, mucoadhesive, polymeric disk that may be formulated to contain and release a desired pharmacologically active agent, such as modafinil. Such disk compositions are typically applied to the mucosa of the cheek where they adhere, dissolve, and release an effective amount of the pharmacologically active agent.

Tablets and other solid or semi-solid formulations that disintegrate or dissolve rapidly in an individual's mouth are useful for providing modafinil "on demand" or "as needed" (pm). Such rapid disintegration or rapid dissolving formulations may eliminate or greatly reduce the use of exogenous water as a swallowing aid. Furthermore, rapid disintegration or rapid dissolve formulations are also particularly useful in treating individuals with swallowing difficulties. For such formulations, a small volume of saliva is usually sufficient to result in tablet disintegration in the oral cavity. The active ingredient (modafinil) can then be absorbed partially or entirely into the circulation from blood vessels underlying the oral mucosa (sublingual and/or buccal mucosa), or it can be swallowed as a solution to be absorbed from the gastrointestinal tract. As noted above, administration via the oral mucosa usually produces a faster onset of action than orally ingested tablets and has the advantage that the active ingredient bypasses the liver and is not inactivated by hepatic first-pass metabolism (see, e.g., Birudaraj et al. *J. Pharm. Sci.*, 94:70-78 (2005); Ishikawa et al., *Chem. Pharm. Bull.* (Tokyo) 49: 230-232 (2001); and Price et al., *Obstet. Gynecol.*, 89: 340-345 (1997)).

Various techniques may be used to formulate fast (or rapid) disintegrating tablets (fast or rapid dissolving tablets) (see, e.g., Allen L V., *Int. J. Pharm. Technol.*, 7: 449-450 (2003); Fu et al., *Crit. Rev. Ther. Drug Carrier Syst.*, 21: 433-476 (2004)). Fast disintegrating tablet technologies may employ lyophilization, molding, sublimation, and compaction. Such technologies include the ZYDIS® (Cardinal Health, Dublin, Ohio) freeze-dried (lyophilized) oral solid dosage form that does not require water as a swallowing aid because it can dissolve on the tongue in less than three seconds. Fast disintegrating tablet properties may be enhanced by such approaches as spray-drying, moisture treatment, sintering, use of sugar-based disintegrants, and taste-masking technologies (Fu et al, *Crit. Rev. Ther. Drug Carrier Syst.*, 21(6): 433-76 (2004)). The technique of direct compression incorporates a superdisintegrant or a highly water-soluble excipient into a formulation to achieve fast tablet disintegration. Direct compression does not require the use of water or heat during the formulation procedure and is the ideal method for moisture- and heat-labile medications. However, the direct compression method is very sensitive to changes in the type and proportion of excipients and in the compression forces used to achieve tablets of suitable hardness without compromising the rapid disintegration characteristics. Specialized packaging methods, such as strip-packaging, may be used to compensate for the extreme friability of such rapidly disintegrating tablets. Examples of useful excipient proportions and other related parameters using a superdisintegrant in order to formulate durable fast-disintegrating tablets for oral administration have been described (see, e.g., Watanabe et al., *Biol. Pharm. Bull.*, 18:1308-1310 (1995); Bi et al., *Chem. Pharm. Bull.* (Tokyo), 44: 2121-2127 (1996)). Accordingly, a fast disintegrating tablet is a particularly useful format as it provides a means for enhanced release of modafinil from the formulation for rapid absorption by tissue and blood vessels that lie under the sublingual mucosa. Such tablets can be made by selecting the appropriate pharmaceutical excipients in the correct proportion in combination with optimal manufacturing techniques and compression parameters.

Another preferred formulation that provides a more efficient and desirable delivery of the modafinil component than swallowing tablets is a nasally (intranasally) administrable delivery form that delivers the modafinil component to the intranasal mucosa for absorption by underlying tissue and blood vessels or a form that delivers modafinil to the lungs for absorption by underlying blood vessels. Preferably, an intranasally administrable delivery form is mucoadhesive. Intranasally administrable forms include formulations that may be applied directly to nasal passages or that may be suspended in a carrier for applying to or spraying (e.g., nebulized) into the nasal passages, such as, without limitation, microparticles, microspheres, gels, liposomes, and micelles (see, e.g., Cilurzo et al., *Eur. J. Pharm. Sci.*, 24(4): 355-361 (2005); Türker et al., *Pharm. World Sci.*, 26(3): 137-142 (2004)). A composition for nasal administration may be provided in the form of a solution, liquid suspension, or powder, which is mixed with a gas (e.g., air, oxygen, nitrogen, etc., or combinations thereof) so as to generate an aerosol or suspension of droplets or particles. Alternatively, a composition for nasal administration of modafinil may be prepared and/or packaged in a manner that permits an individual to inhale (snort) the composition into the nasal passages. Intranasally administrable compositions may be prepared employing techniques known in the art and may include saline, a preservative (e.g., benzyl alcohol), and/or other solubilizing or dispersing agents known in the art. Intranasally administrable compositions may also comprise one or more compounds that enhance transport and absorption of the modafinil component across the nasal mucosa.

A composition comprising modafinil as described herein may also comprise any of a number of various pharmaceutically acceptable carriers (vehicles) or excipients known in the art that may provide one or more beneficial pharmacological or pharmaceutical properties, including but not limited to, more efficient delivery of the modafinil component to the brain and/or central nervous system, less objectionable or less painful administration to an individual, and/or longer storage of compositions (i.e., enhanced shelf-life). Accordingly, pharmaceutical compositions comprising modafinil as described herein may include, without limitation, taste-masking agents (e.g., sweeteners, flavorings), ion exchangers, alumina, aluminum stearate, lecithin, serum proteins (e.g., human serum albumin), buffering agents (e.g., phosphates, citrate, glycine, sorbic acid, potassium sorbate, and the like), partial glyceride mixtures of saturated vegetable fatty acids, water, salts or electrolytes (e.g., protamine sulfate, disodium hydrogen phosphate, potassium hydrogen phosphate, sodium chloride, zinc salts, and the like), colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, lanolin, and combinations thereof.

To mask the taste of modafinil, sweeteners and/or flavoring agents may be used in the compositions described herein, and especially in those compositions that are formulated for administration to the oral or nasal mucosa where absorption takes place during the residence time in the oral or nasal cavities. Flavoring agents useful in the compositions described herein include various natural and artificial flavors, flavor enhancers, and breath fresheners. Common flavoring agents that may be used in the compositions described herein include, but are not limited to, maltol, vanillin, ethyl vanillin, menthol, citric acid, fumaric acid, ethyl maltol, tartaric acid, and combinations thereof. Sweeteners that may be used in compositions described herein include, but are not limited to, one or more of sucrose, calcium saccharinate, ammonium cyclamate, ammonium glycirhizinate, aspartame, glucose, and glucitols such as inositol, mannitol, sorbitol, and dulcitol. Preferably, a taste-masking agent used in a composition described herein comprises one or more sweeteners in combination with one or more flavoring agents. Taste-masking agents may be present in compositions described herein in a variety of ranges, such as in an amount ranging from about 1.0 mg to about 10.0 mg (such as 4.0 mg to 8.0 mg of aspartame), from about 100.0 mg to about 400.0 mg (such as 200.0 mg to 350.0 mg of glucose), from about 200 mg to about 800 mg (such as 300 mg to 700 mg of sorbitol), and from about 5.0 mg to about 50.0 mg (such as 10.0 mg to 30.0 mg of any of a variety of natural or artificial fruit flavors) per unit dosage.

The consistency and viscosity of a composition used in the methods described herein may be controlled by incorporating one or more polymers or hydrogels that absorb water and thereby produce gels of varying viscosity. Hydrogels suitable for use in pharmaceutical preparations are well known in the art (see, e.g., *Handbook of Pharmaceutical Excipients*, (The American Pharmaceutical Association and The Pharmaceutical Society of Great Britain (1986)); *Handbook of Water-Soluble Gums and Resins*, (ed. R. L. Davidson) (McGraw-Hill Book Co., New York 1980)). Hydrogels that may be useful in various compositions described herein include, but are not limited to, hydroxypropyl cellulose, hydroxypropyl methyl cellulose, sodium carboxymethylcellulose ("CMC"), polyacrylic acid, poly(methyl methacrylic acid) ("PMMA"), and combinations thereof. When present, a hydrogel(s) preferably comprises from about 0.1% to about 50% by weight to volume (w/v) of a composition.

Compositions comprising modafinil for use in the methods described herein may be formulated for topical administration. Such topically administrable compositions ("topical formulations") are formulated to promote absorption of modafinil through the dermal layers of an individual into the underlying tissue and then into the systemic blood circulation for delivering to the brain and/or CNS. Topical formulations may be prepared with a suitable ointment, gel, cream, or lotion containing modafinil suspended or dissolved in a carrier. Preferred topical formulations contain a non-particulate form of modafinil. Preferred carriers for topical administration of modafinil include, but are not limited to, mineral oil, liquid petroleum, white petroleum, propylene glycol, polyoxyethylene polyoxypropylene compound, and emulsifying wax. One or more emollients may be present to enhance penetration through the skin. Other suitable carriers may include, but are not limited to, sorbitan monostearate, polysorbate 60, cetyl esters wax, cetearyl alcohol, 2-octyl-dodecanol, and benzyl alcohol. A preferred dosage form for topical administration of modafinil is a transdermal patch containing a topical formulation comprising modafinil as described herein. When such a patch is applied to the skin of an individual, the topical formulation containing modafinil is released and absorbed through the dermal layers. Transdermal patches may include an adhesive tape or an adhesive layer that holds the patch against the skin of an individual while the modafinil component is released and adsorbed through the skin. Transdermal patches may be conveniently packaged and easily opened for use as needed.

Compositions comprising modafinil as described herein may also be formulated as suppositories for insertion into the rectum where a modafinil component of the suppository composition is released for absorption across the mucosa and into the underlying tissue and blood vessels. Methods of preparing suppositories are known in the art. Suppository compositions may be prepared by mixing a modafinil component (modafinil or a modafinil composition described herein) with a suitable non-irritating excipient that is solid at room temperature but liquid at body temperature and, therefore, after insertion into the rectal space will melt and release the modafinil component that can be absorbed across the mucosal tissue and into the underlying blood vessels. Such excipients include, but are not limited to, cocoa butter, beeswax, polyethylene glycols, and combinations thereof.

Pharmaceutical compositions comprising modafinil may be packaged in a variety of ways that are appropriate to the particular dosage form and corresponding mode of administration. Such packaging includes, but is not limited to, vials, bottles, cans, packets, ampoules, cartons, flexible containers, inhalers, nebulizers, and specialized strip packaging. Compositions described herein may be packaged for single or multiple administrations from the same container.

Kits may comprise a modafinil composition as described herein prepared in a form for delivery by an appropriate route along with instructions for administering the composition to treat PE in an individual. For example, a kit may comprise a modafinil-containing composition (e.g., suspension, dry powder, lyophilized form) optionally along with an appropriate pharmaceutically acceptable diluent (e.g., buffer, saline, non-aqueous solvent, etc.) for combination with the modafinil-containing composition shortly before administration by a particular route according to the accompanying instructions.

A variety of devices may be used for administering modafinil to an individual to treat PE in an acute or "as needed" (prn) manner. Devices that may be used for administering modafinil to treat PE in an individual include, without limitation, an inhaler, a nebulizer, and a disposable applicator for applying modafinil directly to a dermal or mucosal surface of the individual. Preferably, such devices deliver to an individual a sufficient amount of modafinil to delay ejaculation by the individual during sexual intercourse within less than 11 hours of administration, more preferably within less than 10 hours of administration, still more preferably within less than 5 hours of administration, yet even more preferably within 1 hour of administration, and most preferably within 30 minutes of administration.

A disposable applicator for applying modafinil to treat PE may take any form that may be used by an individual to apply modafinil to a dermal or mucosal surface of the individual. A disposable applicator may or may not be designed to adhere to or be otherwise affixed to a dermal or mucosal surface to deliver an effective amount of modafinil to an individual. A non-limiting example of an "adherent" form of a disposable applicator is a transdermal patch that is affixed to the skin of an individual to release an effective amount of modafinil to treat PE. "Non-adherent" forms of a disposable applicator are brought into contact with a dermal or mucosal surface of an individual to release and deliver an effective amount of modafinil without the need of affixing the applicator to the surface. Non-adherent forms of a disposable applicator useful in the methods described herein include, but are not limited to, a swab, a sponge, and a strip. Disposable applicators may be constructed with materials that are commonly employed for making medical devices that come into contact with an individual's body. Such materials are preferably inert and non-allergenic or hypoallergenic. Materials that may be used to construct in whole or in part a disposable applicator useful in the methods described herein include, but are not limited to, wood, cotton, cellulose, plastic, metal, nylon, polyester, latex, rubber, fiberglass, glass, and combinations thereof. A sufficient amount of modafinil or a modafinil composition as described herein is present (e.g., coated, impregnated, suspended, adhered, absorbed) on the disposable applicator such that when the applicator is brought into contact with (e.g., affixed to or pressed, rubbed, or wiped against) a dermal or mucosal surface of an individual, an effective amount of modafinil is released from the applicator to delay ejaculation by the individual during sexual intercourse. Preferably, the modafinil present on a disposable applicator as described herein is greater than 50% by weight d-modafinil and more preferably about 100% by weight d-modafinil. The modafinil present on a disposable applicator as described herein is preferably a non-particulate modafinil.

Various antimicrobial agents may also be used in a composition or device as described herein to prevent microbial contamination and degradation of modafinil and any other component of the composition. Such commonly used antimicrobial agents include phenol, benzyl alcohol, meta-cresol, methyl paraben, propyl paraben, benzalconium chloride, and benzethonium chloride. Such agents may be used singly or in combination and are present in a composition described herein at concentrations that will prevent the growth of bacteria, fungi, and/or other microorganisms, but that will not be toxic to the individual who is administered the composition.

As may be required by applicable regulatory standards, compositions described herein are prepared consistent with good manufacturing practices that are currently used in the pharmaceutical industry and that are well known to the skilled practitioner. Further, as may be required, sterile compositions are prepared in accordance with industry and regulatory standards using any of a variety of methods for sterilizing pharmaceutical compositions including, without limitation, ultrafiltration, autoclaving, dry and wet heating, exposure to gases (such as ethylene oxide), exposure to liquids (such as oxidizing agents including sodium hypochlorite), exposure to high energy electromagnetic radiation (such as ultraviolet light, X-rays, gamma rays, and ionizing radiation). Choice of method of sterilization, where required, will be made by the skilled practitioner with the goal of effecting the most efficient sterilization that does not significantly alter the desired pharmacological activity of the modafinil component or any other component of a composition intended for administration to an individual.

As noted above, there are considerable medical and pharmacological data on the safe use of modafinil to treat human individuals for other disorders, most notably, excessive daytime sleepiness (EDS) in individuals who suffer from narcolepsy. Moreover, data presented below, indicate that modafinil has the pharmacological property to delay premature ejaculation (PE) in male human individuals. Additional data regarding the use of modafinil to treat PE as may be required for regulatory approval of specific methods and compositions describe herein may be obtained from further clinical human and animal studies. Established animal models for treating PE offer a highly economical and efficient means for obtaining additional data prior to or in conjunction with human clinical trials required in the process of regulatory approval of a specific methods and composition described herein. Animal models for treatment of PE typically employ male rats and involve monitoring various aspects of male rat sexual behavior including time of ejaculations, erections, and thrusts by the male rats in the presence and absence of various amounts of test compounds or compositions (see, e.g., Looney et al., *Pharmacol. Biochem.* 82: 427-433 (2005); Oliver et al., *Curr. Pharma. Des.*, 11(31): 40694077 (2005); and Waldinger et al., *World J. Urol.*, 23(2): 115-118 (2005)).

In order to more fully illustrate the invention, the following non-limiting examples are provided.

EXAMPLES

Example 1

Delayed Ejaculation with Sublingually Administered D-Modafinil

The synthesis of (d)-(+)-modafinil has been described in the literature (see, e.g., Prisinzano et al., *Tetrahedron Asymmetry*, 15: 1053-1058 (2004); U.S. Pat. No. 4,927,855 ("Lafon synthesis")). In accordance with the Lafon synthesis, the intermediate carboxylic acid was converted to the diastereomic salt mixture with (+)alpha-methylbenzylamine. The diastereomers were separated, and the appropriate chiral acid liberated from the salt form. The acid was converted to the methyl ester via esterification and reacted with ammonia/methanol solution to yield d-modafinil. The enantiomeric purity was in excess of 98%-99%.

Initial formulation tests of modafinil (racemate) and pure d-modafinil revealed a bitter taste. Therefore, the pharmaceutical formulation included one or more taste-masking ingredients. The d-modafinil was mixed with various taste-masking agents, including pulverized mints, breath fresheners, and natural and artificial flavorings.

The synthesized d-modafinil was compounded into a composition containing sugar, spearmint flavor, cinnamon flavor, gum arabic, gelatin, corn syrup, and dyes that could be administered sublingually. Formulations containing 100 mg of d-modafinil were prepared.

Subject 1 took the above-described formulation of d-modafinil sublingually at 9:00 pm in the course of testing a composition containing d-modafinil for a different effect unrelated to sexual activity. Subject 1 reported that unexpectedly the time to ejaculate during sexual activity was significantly longer than usual by a factor of about two to three times. A week later, Subject 1 took the formulation sublingually for a second time and, again, reported that the time to ejaculate during sexual intercourse was significantly delayed by a factor of approximately two to three times.

The data demonstrate that sublingual administration of d-modafinil can provide a desirable delay of ejaculation during sexual activity, that the effect is drug-dependent, and that the effect is reversible.

Example 2

Delayed Ejaculation with Orally Administered (Tablet) Racemic Modafinil

Subject 2 took racemic modafinil (200 mg) in the form of an orally administrable tablet of PROVIGIL® (Cephalon) at 3:00 pm for the purpose of increasing alertness. Hours later, Subject 2 reported that he unexpectedly experienced a delay in ejaculation during sexual activity.

CONCLUSION

Example 1 employed sublingual administration of a short-term, rapid-onset formulation of d-modafinil. Example 2 employed oral administration of a longer onset, longer lasting tablet formulation of racemic modafinil. Taken together, the results of the above Examples demonstrate that the pharmacological activity of modafinil to delay ejaculation during sexual activity may be effectively provided by a range of compositions, formulations, and routes of administration.

All patents, applications, and publications cited in the above text are incorporated herein by reference.

Other variations and embodiments of the invention described herein will now be apparent to those of skill in the art without departing from the disclosure of the invention or the claims below.

The invention claimed is:

1. A method of treating premature ejaculation in a male individual comprising administering to the individual a pharmaceutical composition comprising the active ingredient modafinil and a pharmaceutically acceptable carrier, wherein said modafinil is present in an amount effective to delay ejaculation during sexual intercourse.

2. The method according to claim 1, wherein said modafinil is selected from the group consisting of d-modafinil, 1-modafinil, racemic modafinil, and combinations thereof.

3. The method according to claim 2, wherein said modafinil is d-modafinil.

4. The method according to claim 2, wherein said combination of 1-modafinil and d-modafinil is greater than about 50% by weight d-modafinil.

5. The method according to any one of claims 1-4, wherein said modafinil is a non-particulate form of modafinil.

6. The method according to claim 1, wherein said pharmaceutical composition further comprises an ingredient selected from the group consisting of buffering agent, a plasticizing agent, a mucoadhesive compound, a stabilizing agent, a taste-masking agent, a flavoring agent, a coloring agent, an antiseptic, an inert filler agent, a preservative, and combinations thereof.

7. The method according to claim 1, wherein said pharmaceutical composition is administered to the individual by a route of administration selected from the group consisting of oral, sublingual, buccal, nasal, intravenous, subcutaneous, intramuscular, topical, and rectal.

8. The method according to claim 7, wherein the route of administration is sublingual.

9. The method according to claim 7, wherein the route of administration is buccal.

10. The method according to claim 7, wherein the route of administration is nasal.

11. The method according to claim 1, wherein the pharmaceutical composition is formulated as a fast-disintegrating tablet or as a film.

12. The method according to claim 11, wherein said film is a mucoadhesive film.

* * * * *